(12) United States Patent
Duncan

(10) Patent No.: US 8,157,664 B2
(45) Date of Patent: Apr. 17, 2012

(54) ASSIST DEVICE

(75) Inventor: Michael Wayne Duncan, Lake City, MN (US)

(73) Assignee: Even Par Enterprises, Inc., Lake City, MN (US)

( * ) Notice: Subject to any disclaimer, the term of this patent is extended or adjusted under 35 U.S.C. 154(b) by 0 days.

(21) Appl. No.: 12/631,374

(22) Filed: Dec. 4, 2009

(65) Prior Publication Data
US 2010/0145474 A1 Jun. 10, 2010

Related U.S. Application Data

(60) Provisional application No. 61/200,972, filed on Dec. 5, 2008.

(51) Int. Cl.
*A63B 69/36* (2006.01)
*A61F 2/80* (2006.01)

(52) U.S. Cl. .......... 473/212; 473/205; 473/276; 623/33; 623/65

(58) Field of Classification Search ................. 473/203, 473/204, 205, 206, 212, 213, 276, 549, 568
See application file for complete search history.

(56) References Cited

U.S. PATENT DOCUMENTS

| | | | |
|---|---|---|---|
| 7,626 A | 9/1850 | Welch | |
| 1,200,403 A * | 10/1916 | Weyer | 362/103 |
| 1,320,934 A * | 11/1919 | Schopp | 362/103 |
| 2,697,436 A | 12/1954 | Coston | |
| 2,763,264 A | 9/1956 | McInnemy | |
| 3,242,923 A | 3/1966 | Jacoby | |
| 3,556,092 A | 1/1971 | Eisenberg | |
| 3,640,273 A | 2/1972 | Ray | |
| D234,434 S | 3/1975 | Trevino | |
| 3,896,799 A | 7/1975 | Seeley | |
| 3,942,194 A * | 3/1976 | Winter | 623/65 |
| 4,000,769 A | 1/1977 | Katz | 206/316.2 |
| 4,203,495 A * | 5/1980 | Crownover | 172/370 |
| 4,245,841 A * | 1/1981 | Owens, Jr. | 473/212 |
| 4,265,232 A | 5/1981 | Stonich | |
| 4,315,504 A | 2/1982 | Drennan et al. | |
| 4,445,686 A * | 5/1984 | Daugherty | 473/464 |
| D292,128 S | 9/1987 | Thibodo, Jr. | |
| D293,933 S | 1/1988 | Hubbard et al. | |
| D294,176 S | 2/1988 | Tyo | |
| 4,766,890 A | 8/1988 | Hollrah | |
| 4,928,678 A | 5/1990 | Grim | |
| 4,941,479 A | 7/1990 | Russell et al. | |
| 4,974,762 A * | 12/1990 | Boretsky et al. | 224/148.5 |
| 4,996,979 A | 3/1991 | Grim et al. | |
| D318,125 S | 7/1991 | Miller | |
| 5,121,743 A | 6/1992 | Bishop | |
| 5,173,967 A | 12/1992 | Carter | |
| D333,520 S | 2/1993 | Mann | |
| 5,203,766 A | 4/1993 | Carter et al. | |
| 5,263,497 A | 11/1993 | Grabenkort et al. | |
| D345,421 S | 3/1994 | Schumann et al. | |

(Continued)

OTHER PUBLICATIONS

U.S. Appl. No. 29/339,503, filed Jul. 1, 2009.

*Primary Examiner* — Nini Legesse
(74) *Attorney, Agent, or Firm* — Christopher J. Volkmann; Westerman, Champlin & Kelly, P.A.

(57) ABSTRACT

A gripping assist device is removably attachable to the forearm of a user. The assist device has a sleeve with an opening sized to receive a handle or grip of an item.

11 Claims, 12 Drawing Sheets

U.S. PATENT DOCUMENTS

| | | | |
|---|---|---|---|
| 5,413,120 A | 5/1995 | Grant | |
| 5,435,013 A | 7/1995 | Davis | |
| 5,445,385 A * | 8/1995 | Brooks | 473/214 |
| D362,542 S | 9/1995 | Richards et al. | D3/218 |
| 5,478,083 A * | 12/1995 | Foster, II | 473/226 |
| D366,758 S | 2/1996 | Weiler | D3/219 |
| D367,535 S | 2/1996 | Stenberg | |
| 5,557,805 A | 9/1996 | Emerson | |
| D374,767 S | 10/1996 | Leach | D3/218 |
| 5,601,356 A * | 2/1997 | McWilliams | 362/103 |
| D382,344 S | 8/1997 | Swedberg et al. | |
| 5,655,221 A | 8/1997 | Worischeck | |
| 5,702,355 A | 12/1997 | Repice et al. | |
| 5,722,092 A | 3/1998 | Borzecki et al. | |
| D397,222 S | 8/1998 | Humensky | |
| 5,827,207 A | 10/1998 | MacMorran | |
| 5,845,643 A | 12/1998 | Vergano et al. | |
| 5,890,809 A * | 4/1999 | Nelson | 383/40 |
| D411,301 S | 6/1999 | Hampson et al. | |
| D413,430 S | 9/1999 | Granata | D3/10 |
| 5,950,626 A | 9/1999 | Wagener et al. | |
| 5,974,586 A | 11/1999 | Reinoso | |
| D420,216 S | 2/2000 | Birkbeck | D3/215 |
| 6,035,442 A | 3/2000 | Marando | |
| 6,062,700 A * | 5/2000 | Price | 362/103 |
| D427,383 S | 6/2000 | Inman | |
| 6,110,135 A | 8/2000 | Madow et al. | |
| D439,039 S | 3/2001 | Austin | D3/228 |
| D441,082 S | 4/2001 | Ruscitti | |
| 6,245,114 B1 * | 6/2001 | Marron | 623/65 |
| D444,563 S | 7/2001 | Rodgers | |
| 6,269,990 B1 * | 8/2001 | Gray | 224/200 |
| 6,350,206 B1 * | 2/2002 | Lambert, ll | 473/205 |
| D455,901 S | 4/2002 | Snider | |
| 6,405,731 B1 | 6/2002 | Chiang | |
| 6,508,205 B1 | 1/2003 | Zink | |
| 6,569,110 B2 | 5/2003 | Bernard et al. | |
| D477,088 S | 7/2003 | Brown et al. | |
| D477,409 S | 7/2003 | Mills et al. | |
| D495,420 S | 8/2004 | Katz et al. | |
| D498,920 S | 11/2004 | Ambrose | D3/219 |
| 6,813,779 B1 | 11/2004 | Williams | |
| D500,352 S | 12/2004 | Sullivan | |
| 6,923,780 B2 | 8/2005 | Price et al. | |
| 6,971,562 B2 * | 12/2005 | Willows et al. | 224/148.4 |
| D515,745 S | 2/2006 | Leyva | |
| 7,097,571 B2 | 8/2006 | Kraus | |
| 7,128,656 B1 | 10/2006 | Orchel | |
| 7,237,703 B1 * | 7/2007 | Nathan et al. | 224/148.5 |
| D549,348 S | 8/2007 | Przybycien | |
| D558,883 S | 1/2008 | Ortiz | |
| D560,041 S | 1/2008 | Cook et al. | |
| D562,549 S | 2/2008 | Bodnar | D3/222 |
| D565,189 S | 3/2008 | Gramza et al. | |
| D569,983 S | 5/2008 | Ellis et al. | |
| D581,539 S | 11/2008 | Rotter et al. | |
| 7,458,947 B2 | 12/2008 | Farrell et al. | |
| 7,465,283 B2 | 12/2008 | Grim et al. | |
| D588,704 S | 3/2009 | Duplessie | |
| D603,969 S | 11/2009 | Bauerfeind et al. | |
| D608,895 S | 1/2010 | Farrell et al. | |
| D617,464 S | 6/2010 | Weaver et al. | |
| D621,943 S | 8/2010 | Marino | |
| D625,376 S | 10/2010 | Marabellas | |
| D627,073 S | 11/2010 | Nace | |
| D634,851 S | 3/2011 | Chiang | |
| D635,269 S | 3/2011 | Franke et al. | |
| D639,048 S | 6/2011 | Bussard | D3/221 |
| D642,280 S | 7/2011 | Goumas | |
| 2001/0022161 A1 * | 9/2001 | Macedo et al. | 119/796 |
| 2002/0077573 A1 | 6/2002 | Bernard et al. | |
| 2004/0214652 A1 * | 10/2004 | Robbins | 473/276 |
| 2005/0077742 A1 | 4/2005 | Wilson | |
| 2005/0101897 A1 | 5/2005 | Froom | |
| 2006/0069335 A1 | 3/2006 | Fritsch et al. | |
| 2006/0094999 A1 | 5/2006 | Cropper | |
| 2006/0173390 A1 | 8/2006 | Van Wyk et al. | |
| 2007/0021228 A1 * | 1/2007 | Flood | 473/226 |
| 2007/0276303 A1 | 11/2007 | Jenner, Jr. | |
| 2008/0127459 A1 | 6/2008 | Burke et al. | |
| 2010/0083415 A1 | 4/2010 | Beckford | |

\* cited by examiner

ASSIST DEVICE

CROSS-REFERENCE TO RELATED APPLICATION

The present application is based on and claims the benefit of U.S. provisional patent application Ser. No. 61/200,972, filed Dec. 5, 2008, titled ASSIST DEVICE, the content of which is hereby incorporated by reference in its entirety.

BACKGROUND

The present application is generally related to devices for assisting those who have difficulty grasping items. More specifically, the present application relates to an assist device that can be removably attached to a user's forearm and can be used to secure a handle, or other item.

There are currently many individuals who lack the arm and/or hand strength required to grip certain items. For instance, it takes a certain amount of arm and hand strength to adequately grip a sports club, such as a golf club, a baseball bat, etc. Many individuals lack sufficient strength. In addition, such individuals may find it difficult to grip other items as well, such as broom handles, rake handles, pan handles, or a wide variety of other things.

There are myriad causes for this reduced grip strength. Among those are included arthritis and rheumatism, which cause joint pain during certain types of flexion or extension of the hand joints, for instance. For example, one study, even several years ago, has indicated that those suffering from arthritis, in the United States alone, number in excess of 51 million. Other things also make it difficult for certain individuals to grip items. Those things include stroke, which afflicts approximately 600,000 people in the United States every year, amputation for various reasons, which afflicts in excess of 185,000 people in the United States every year, diseases such as Cerebral Palsy which afflicts over half a million in the United States, and other causes such as Carpal Tunnel Syndrome which afflicts in excess of 11 million people in the United States.

All of these things can afflict individuals in a way that makes it difficult, or impossible, for those individuals to carry on even simple everyday tasks, much less to engage in hobby activities, such as sports activities.

SUMMARY

A gripping assist device is removably attachable to the forearm of a user. For example, in one embodiment the assist device can be attached to an inner, outer, and/or side of a forearm of the user. The assist device has a sleeve with an opening sized to receive a handle or grip of an item. In one example, a portion of the item (e.g., the handle or grip) is grasped by the user (e.g., using a hand of the user). In another example, the user can move, manipulate, and/or use the item without grasping the item (i.e., the user's hand does not grasp the item).

In one embodiment, the opening is reinforced to retain its shape even when no handle or grip is inserted therein. This makes it easier to insert a handle or grip, into the pouch.

In another embodiment, the opening to the pouch is preformed in a desired shape. The removable attachment to the forearm can be accomplished using straps with attachment elements, such as hook and loop fabric, buckles, snaps, etc.

In another embodiment, the straps can be removably inserted through channels in the forearm contacting portion and/or through buckles attached to the forearm contacting portion of the assist device. In this way, the straps can be reversed to accommodate either a left arm or a right arm, and the straps can be removed and replaced with either longer or shorter straps to accommodate forearms of varying size.

DETAILED DESCRIPTION

Figure 1:
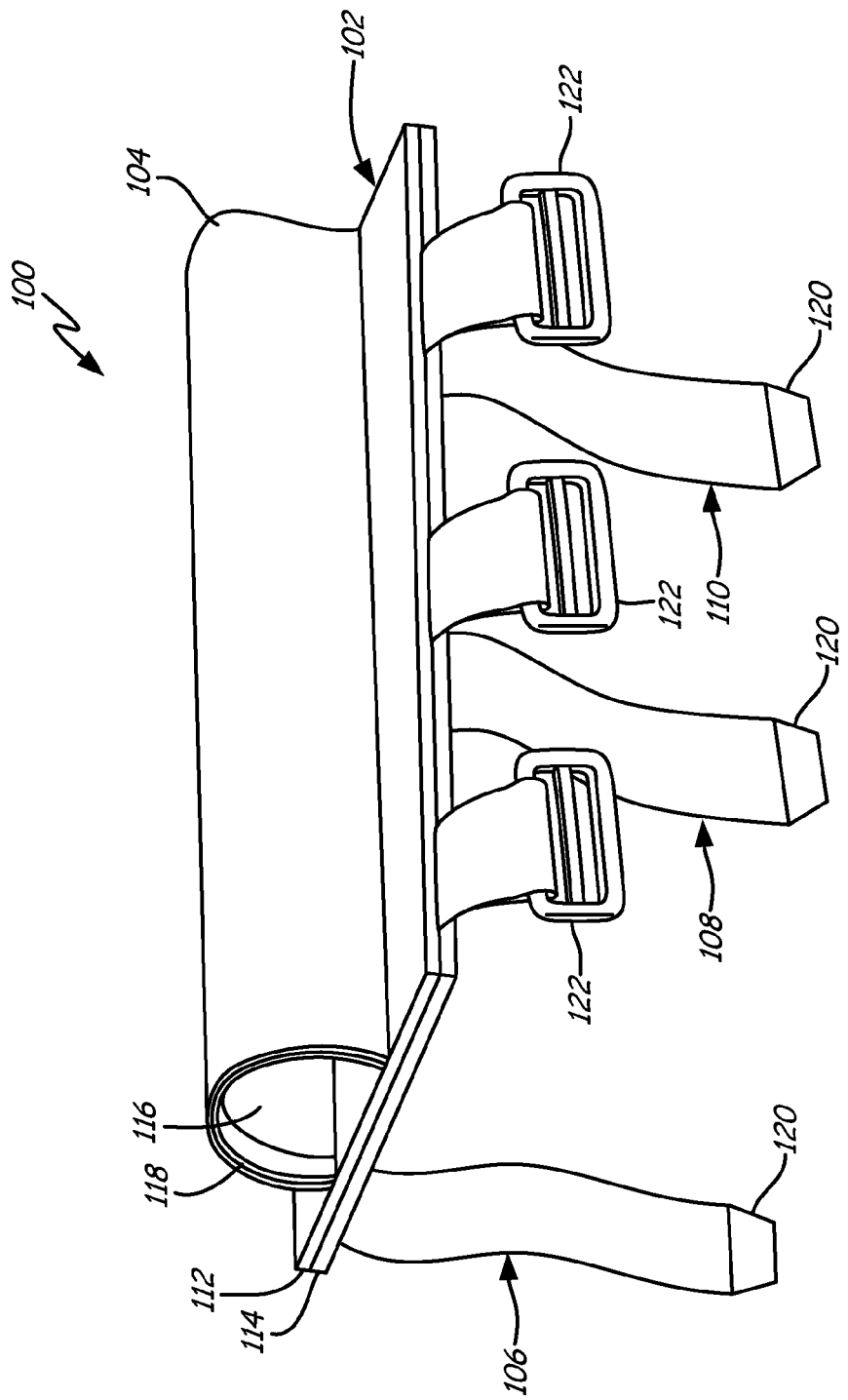
FIG. 1 is a perspective view of an assist device in accordance with one embodiment.

FIG. 1 is a perspective view of an assist device 100 that assists a user in grasping or manipulating an item with a handle. Assist device 100 includes a forearm engaging portion 102, pouch or sleeve 104, and fastening straps 106, 108 and 110.

In the embodiment shown in FIG. 1, portion 102 is formed of two layers of material 112 and 114 which are fastened together. Straps 106-110 are fastened between layers 112 and 114. In one embodiment, portion 102 can include a third layer positioned between layers of material 112 and 114. The third layer can comprise a partial layer of material that creates channels for receiving straps 106-110 therein. In this embodiment, the partial third layer comprises a spacing layer between layer material 112 and 114 for accommodating straps 106-110 between layers of material 112 and 114. In one embodiment, layers 112 and 114 are sewn together and straps 106-110 are sewn between the layers. Of course, device 100 may include only a single layer comprising forearm engaging portion 102, and straps 106-110 can be fastened to device 100 in a different way, such as by stitching, gluing, being formed integrally with portion 102, etc.

Also in the embodiment shown in FIG. 1, pouch 104 includes a handle receiving opening 116 that is sized to receive handles of interest to the user. The handles of interest may include, for instance, the grip of a golf club or a softball or baseball bat, a pan handle, a paint brush, a rake, or shovel handle, a broom handle, etc.

In any case, in one embodiment, the opening 116 is illustratively formed such that it retains its shape, even when no grip or handle is inserted through it, within pouch 104. In the embodiment shown in FIG. 1, opening 116 is defined by a reinforcement element 118, which is formed of a material that has greater rigidity than the material used to form the remainder of pouch 104. Reinforcement element 118, may, for instance, be formed of rubber, plastic, leather, or any type of material which defines opening 116 and has greater resistance to collapsing than the material used to form pouch 104. Of course, pouch 104 can be formed of a less stiff material, such as a thin leather, vinyl, or any other desired material.

In another embodiment, reinforcement element 118 can be removable or fitted to receive inserts that define a different sized opening 116. Therefore, a single assist device 100 can be used to accommodate a wide variety of handles (e.g., a baseball bat and a paint brush) simply by switching inserts to define openings 116 of different sizes. Similarly, element 118 can be configured, using a screw, slip knot, or other mechanism, so it can be re-sized by the user to make opening 116 larger or smaller. Of course, element 118 can be of fixed size, without inserts, as well. Also, element 118 can be eliminated if the material forming pouch 102 is sufficiently rigid so opening 116 stays open when pouch 102 is empty.

In the embodiment shown in FIG. 1, straps 106-110 are fixedly attached to device 100. Straps 106-110 illustratively include tab portions 120 and buckle portions 122. In one embodiment, tab portions 120 are relatively stiff portions (such as stuff plastic or rubber) that can be grasped by the user's free hand, or by the user's teeth, or in any other desired way. The straps also illustratively include hook and loop fabric, or another releasable fastening mechanism, such that when they are threaded through buckles 122, tab 120 can be folded back along straps 106-110 to releasably attach the portions of straps 106-110 together to hold the user's forearm therein. This is described in greater detail below.

It will be appreciated, of course, that the specific materials from which device 100 is made, and the specific way in which those materials are connected to one another, is not critical to the present invention. Device 100 can be made using a wide variety of different material and connecting those materials to one another in a wide variety of different ways. In addition, the portions of device 100 can be made integrally with one another, such as by molding, extrusion, or any other desired process.

FIGS. 2-5 show one embodiment illustrating how a user fastens assist device 100 to the inner forearm. While embodiments of the assist device described herein are illustrated and discussed in the context of use on an inner forearm, it is noted that the assist device can be attached to an outer forearm and/or a side of a forearm of the user, for example.

Further, in one illustrative embodiment the assist device is positioned such that the user grasps a portion of the item (e.g., a handle or other portion of the item that extends from the assist device). For example, if the assist device is worn on a left forearm the user grasps the item using the user's left hand. In accordance with one embodiment, the assist device can be used without the user grasping the item. For instance, in the above example the user can move, manipulate, and/or use the item without grasping the item in the user's left hand. It is noted that these are examples illustrating how the assist device can be utilized by a user and are not intended to limit the scope of the concepts described herein.

Figure 2:
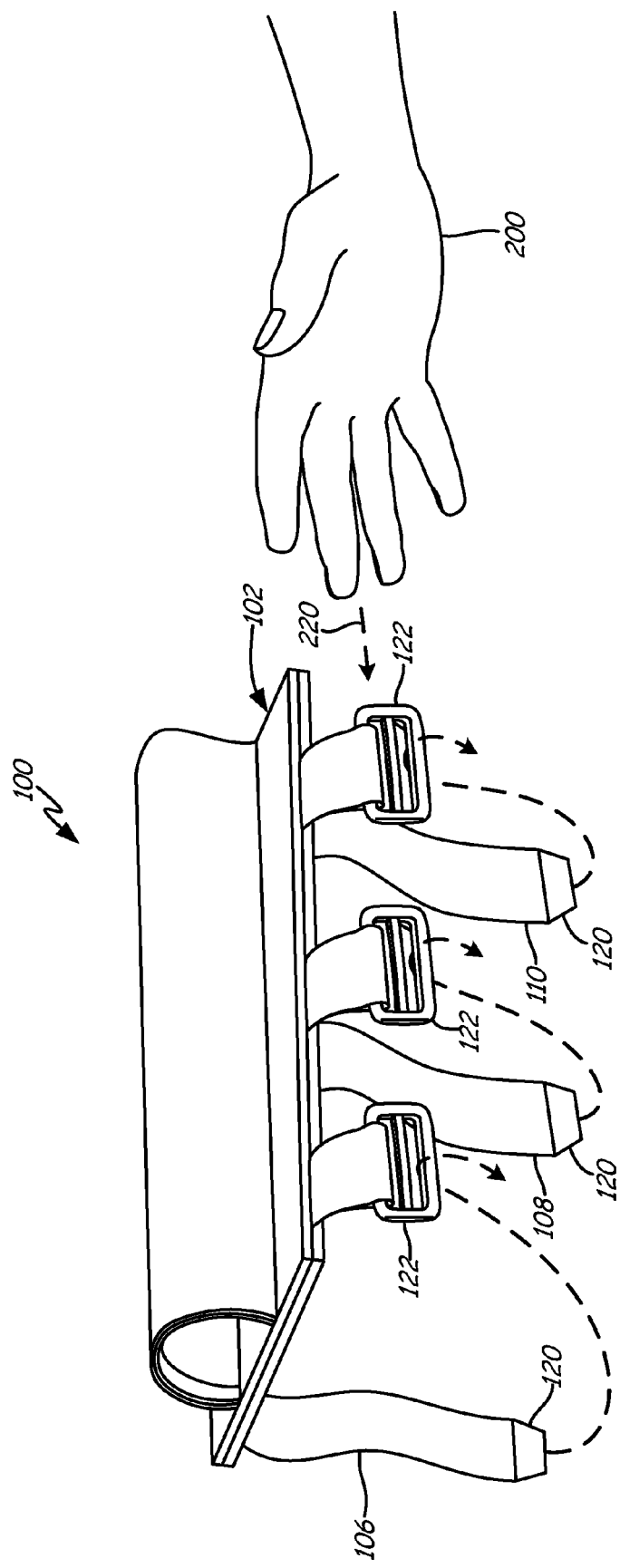
FIG. 2 shows an assist device relative to a user's hand.

FIG. 2 shows that, in one embodiment, tabs 120 of straps 106-110 are first inserted through one of the openings in buckles 122. The tabs 120 are folded back along each of the straps 106-110 to form a loose ring such that a user's hand 200 can fit through the ring.

Figure 3:
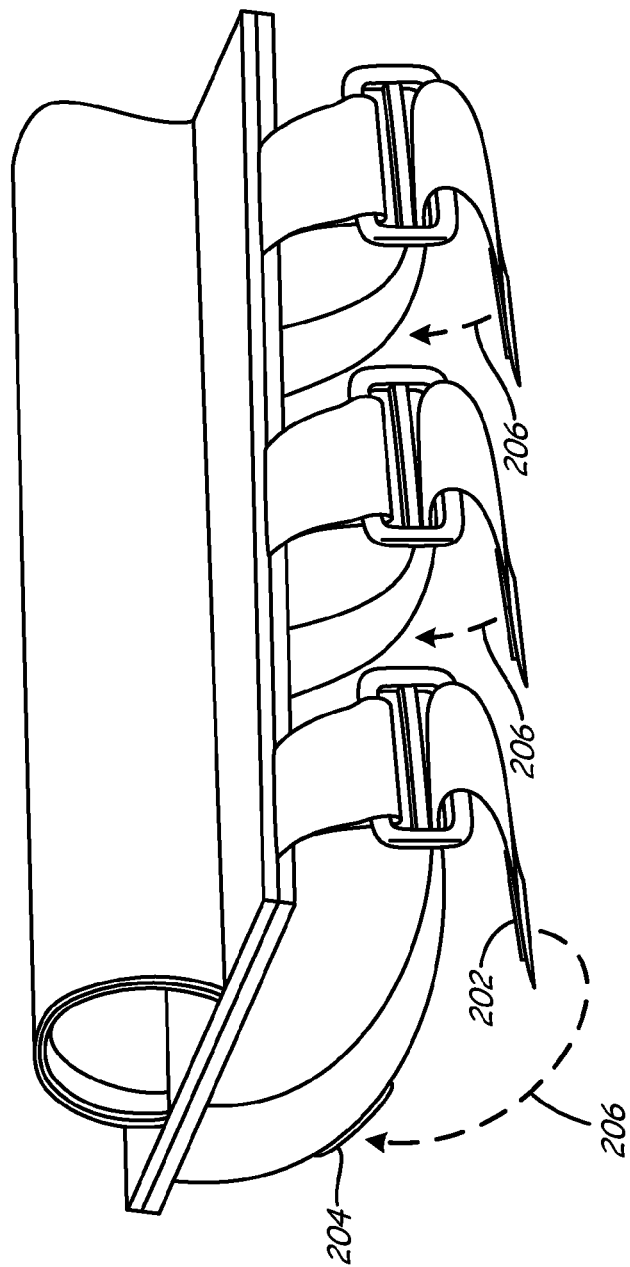
FIGS. 3-5 illustrate one embodiment of how the assist device is removably attached to a user's inner forearm.

FIG. 3 illustrates this in more detail. As shown in FIG. 3, a distal portion of straps 106-110 is provided with one part 202 of a fastening mechanism, such as hook and loop fabric. A more proximal portion of straps 106-110 is provided with another portion 204 of the fastening mechanism, such as hook and loop fabric. It will, of course, be appreciated that, instead of using hook and loop fabric, any other desired fastening mechanism can be used as well. The embodiment shown in FIG. 3 is described with respect to hook and loop fabric for the sake of simplicity only.

Each of straps 106-110 is inserted through its corresponding buckle 122 and folded back on itself as shown by arrows 206 in FIG. 3.

Figure 4:
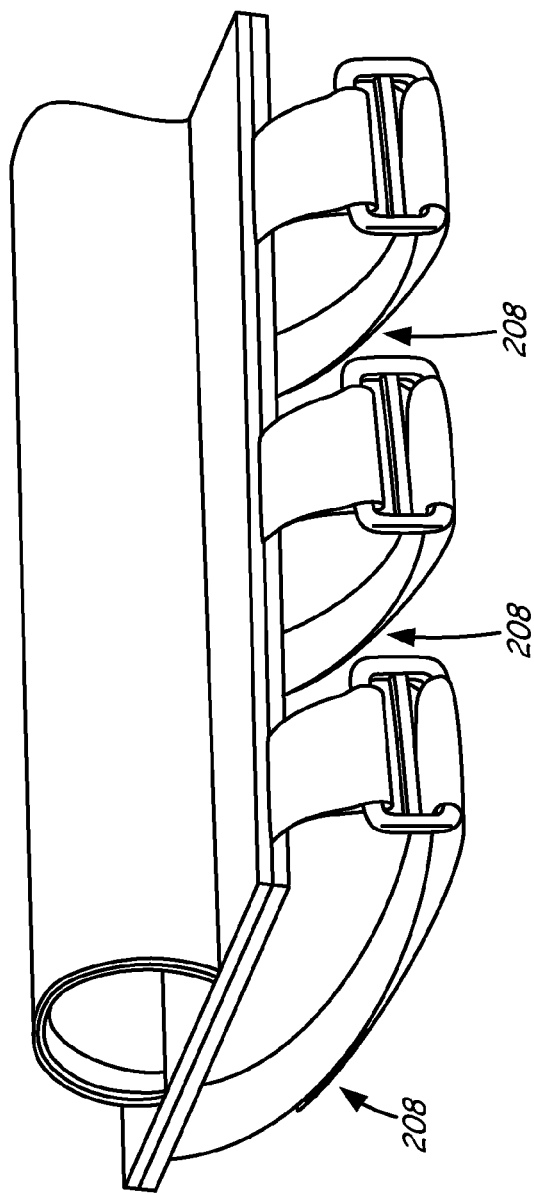

FIG. 4 shows that this results in each of the straps 102-106 defining a loose loop. In one embodiment, this is accomplished by pressing the fastening mechanisms 202 and 204 against one another in the direction generally indicated by arrow 208 in FIG. 4. The loose loops are illustratively sized to receive the hand 200 of the user therethrough.

Figure 5:
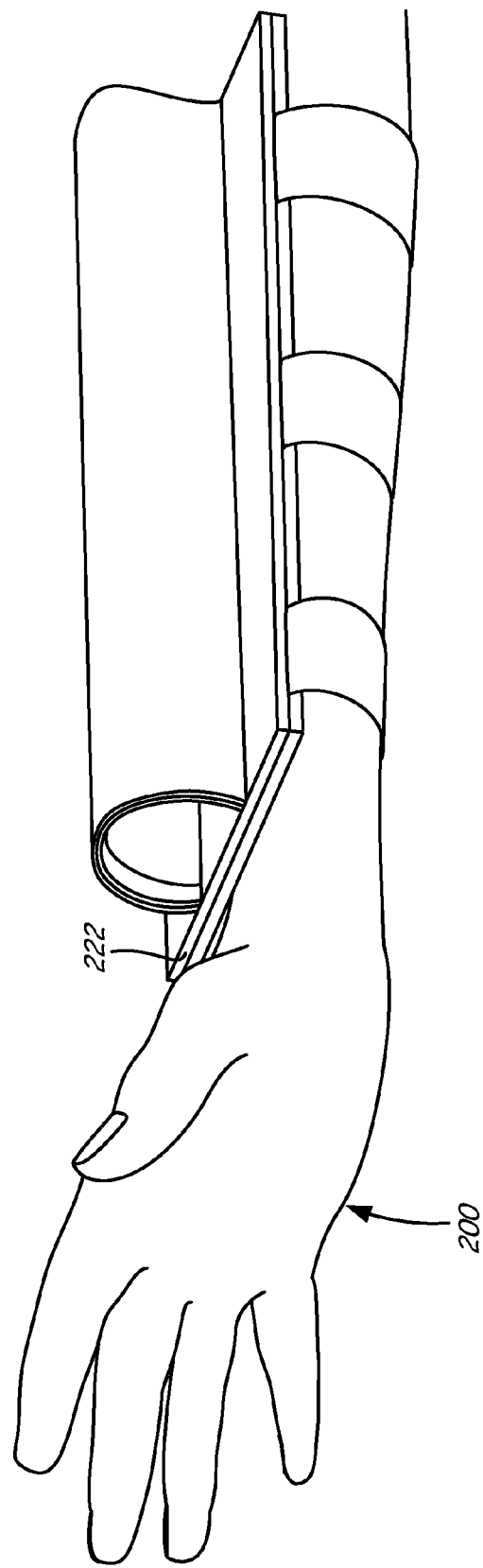

Referring again to FIG. 2, the user then inserts his or her hand 200 through the loose loops defined by straps 106-110 by advancing the hand 200 (relative to device 100) in the direction generally indicated by arrow 220 in FIG. 2. The user illustratively advances his or her hand 200 in the direction indicated by arrow 220 to a point where the base of the palm (such as the base of the thenar pad region) is substantially adjacent an end 222 of device 100 as shown in FIG. 5. In one embodiment, the user positions hand 200 such that the hand can be bent, at the wrist, through a substantial amount of flexion and extension, without being significantly inhibited by device 100.

The user then illustratively tightens straps 106-110 such that they are securely fitted around the user's inner forearm in the position shown in FIG. 5. This can be done, for instance, by the user taking tab 120 in his or her teeth, tightening the strap, and then pressing the connection mechanisms 202-204 back together again.

It will also be noted, of course, that the connection of device 100 with the user's forearm can be accomplished in many different ways. For instance, buckles 122 can be formed such that, when straps 106-110 are threaded therethrough, they can be tightened, but then the straps frictionally engage the buckle so that they will not loosen, unless the user manipulates the buckle in some way. These types of buckles are known. There are a wide variety of different buckles, snaps and connection mechanisms which can be used to fasten device 100 to the user's forearm.

It will also, of course, be noted that the user need not have multiple straps 106-110. Instead, device 100 may have a single sleeve (with hook and loop fabric or another fastening device) which is wrapped around the user's forearm, in order to hold device 100 snuggly against the user's forearm, in a removable connection. Further, instead of having straps or a sleeve with different connections, a resilient cuff can be used in which case the user can simply slide his or her arm through the cuff and it will resiliently (or elastically) form to the contours and surface of the user's forearm, thus holding device 100 snuggly against the user's forearm. Such a cuff can be made of, for instance, neoprene, an elastic material, or any other type of resilient material which has a memory such that, even through it is stretched to insert the user's hand and forearm therethrough, it will close on the user's forearm, elastically or resiliently, in an attempt to retain its original size, thus fastening device 100 to the user's forearm. Of course, a wide variety of other attachment mechanisms can be used as well.

In any case, FIG. 5 shows that device 100 is attached to the user's inner forearm.

Figure 6:
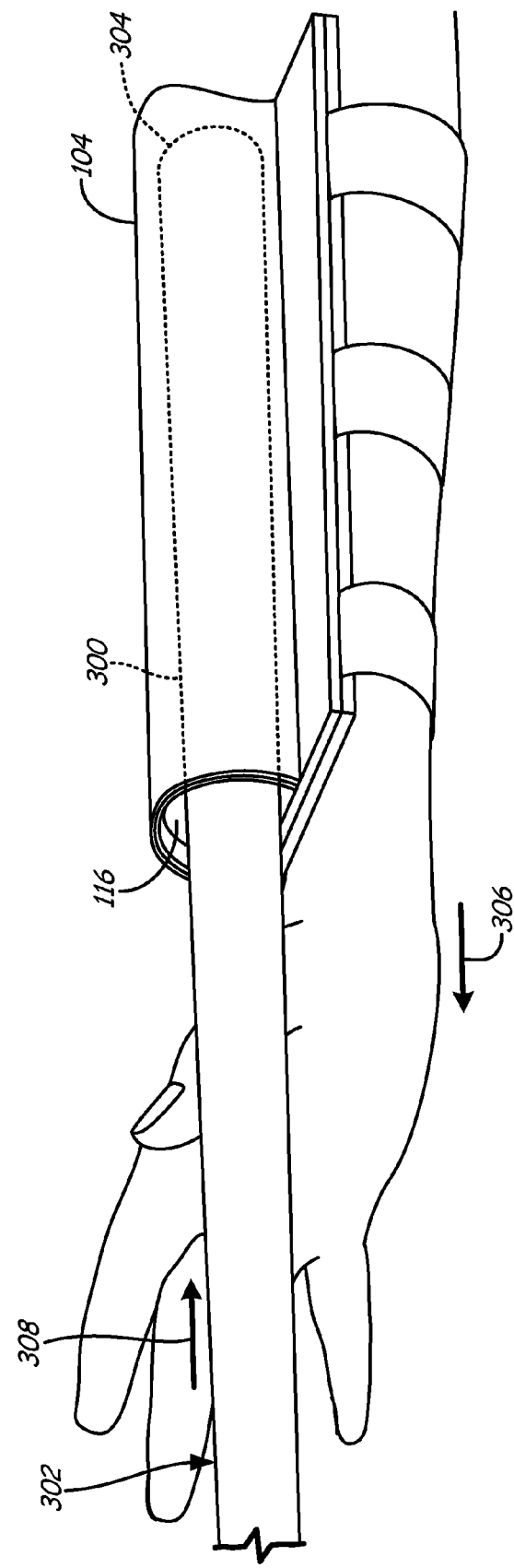
FIG. 6 illustrates one embodiment in which a grip or handle of an item to be grasped is inserted by a user into the assist device.

The user is then ready to insert a device to be grasped within pouch 104. FIG. 6 shows one embodiment for doing this. FIG. 6 shows the grip 300 of a golf club 302 inserted within pouch 104. In order to do this, in accordance with one embodiment, the user first places the head of the golf club on the ground and then positions the opening 116 of pouch 104 closely adjacent end 304 of grip 300. The user then advances his or her hand (which now has device 100 snuggly attached to it) in the direction generally indicated by arrow 306, relative to golf club 302. This causes golf club 302 to move, relatively speaking, in the direction indicated by arrow 308 such that end 304 of grip 300 passes through opening 116 and advances within pouch 104, as shown in FIG. 6. The user can then grasp the shaft of golf club 102. It will also be noted of course, that golf club 302 can have pouch 104 sized such that a portion of the grip 300 sticks out through opening 116 so the user can actually grasp the grip portion of the golf club, instead of the shaft portion.

Figure 7:
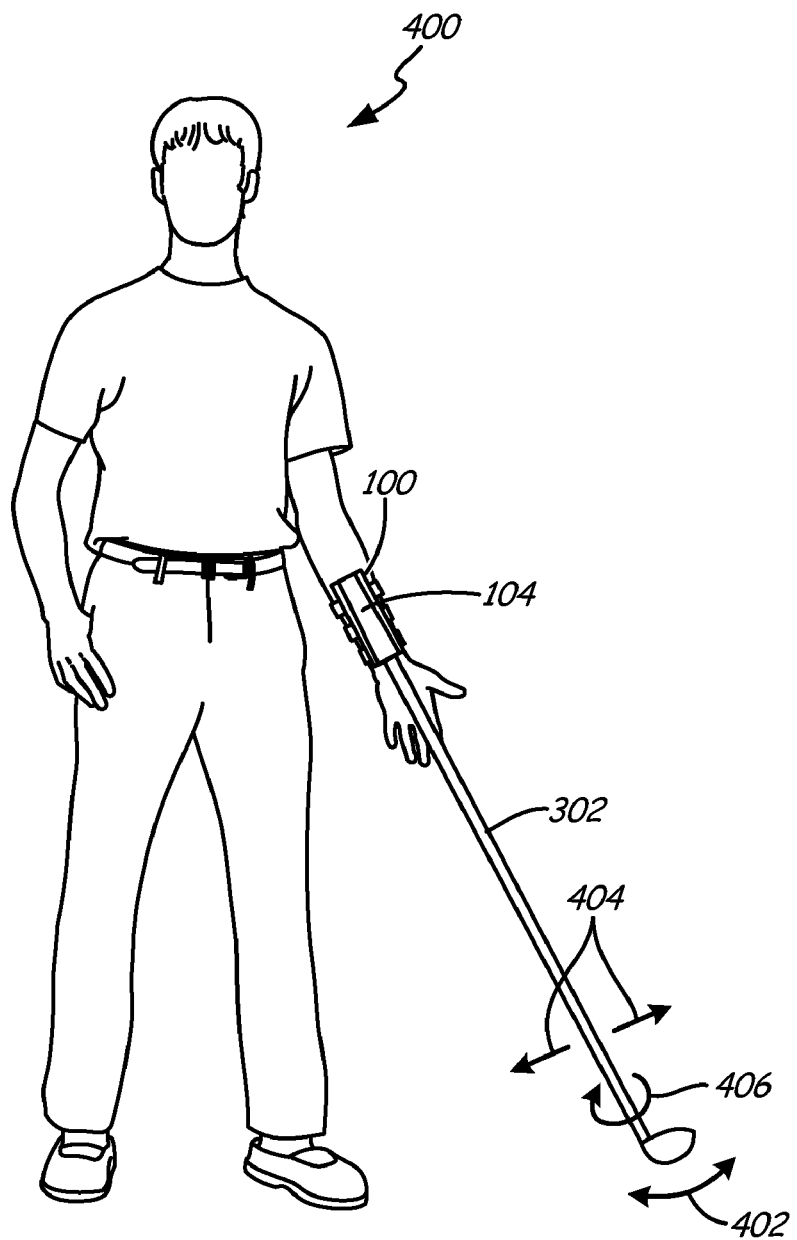
FIG. 7 shows a user, with an assist device removably attached to the inner forearm, and a sports club inserted therein.

FIG. 7 illustrates a user 400 having device 100 attached to the inner forearm of the user, with golf club 302 fit within pouch 104. In one embodiment, the size of pouch 104 is sufficient to lightly, frictionally, engage at least a portion of grip 300 therein. This provides some stability. By grasping golf club 302, user 400 can then swing the head of golf club 302 up and down vertically generally in the direction indicated by arrow 402, side-to-side generally indicated by arrows 404, or rotationally, generally indicated by arrow 406.

Figure 8:
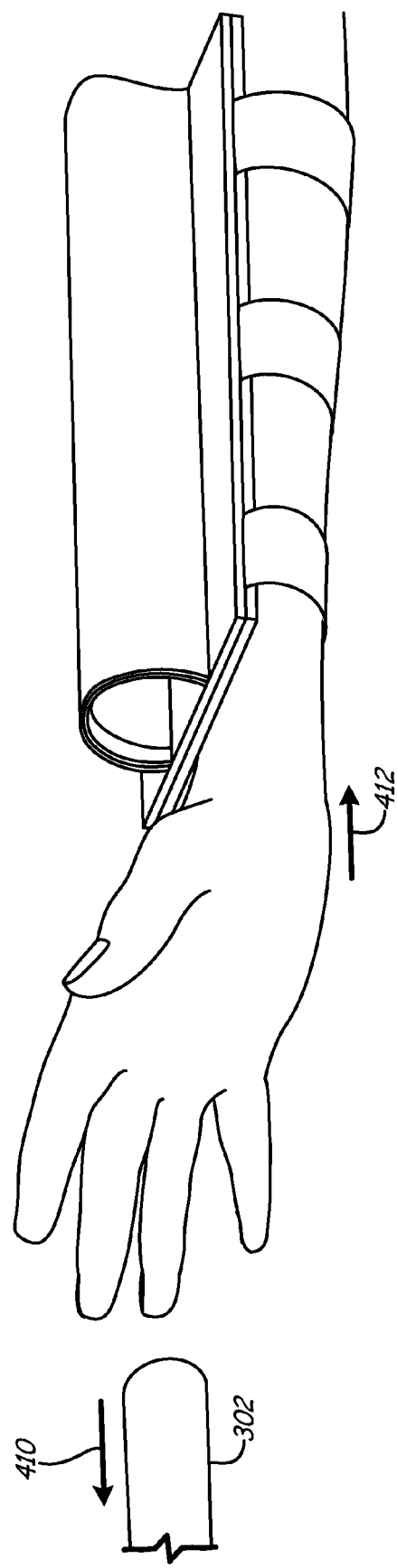
FIG. 8 illustrates how the grip or handle can be extracted from the assist device.

When the user is finished with golf club 302, the user simply withdraws golf club 302 from pouch 104. One embodiment of this is indicated by FIG. 8. FIG. 8 shows that, in order to release the golf club from pouch 104, the user simply moves the golf club 302 and the user's forearm (with device 100) relative to one another in the directions generally indicated by arrows 410 and 412. This causes the grip 300 of golf club 302 to be extracted from within pouch 104.

Figure 9:
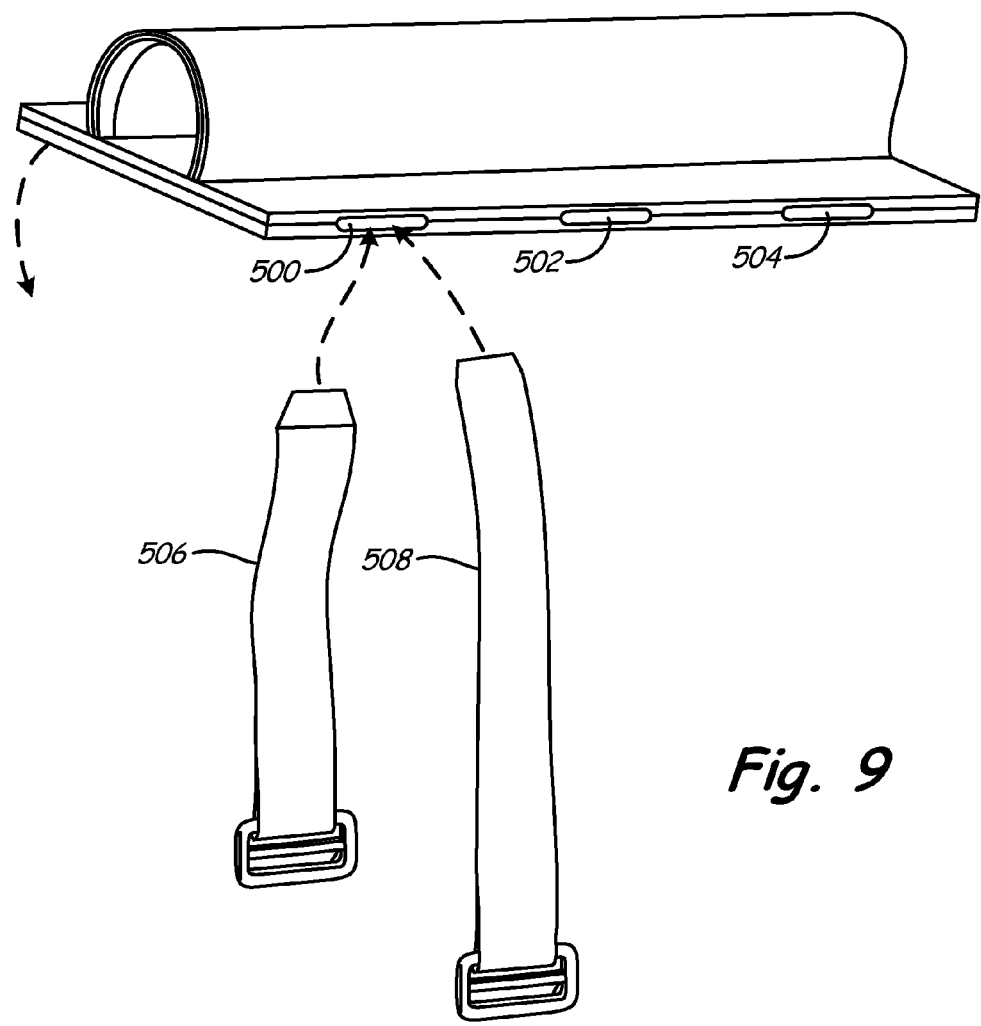
FIG. 9 illustrates an embodiment of the assist device in which channels are used to receive fastening straps.

FIG. 9 shows another embodiment of device 100 in which, instead of fixedly attaching straps 106-110 to device 100, a plurality of channels 500, 502 and 504 are provided in portion 102 of device 100. The channels are sized to slidably receive straps 506 and 508 therethrough. This allows different size straps 506 and 508 to be inserted through channels 500-504, in order to accommodate different size forearms. Multiple sets of straps of different size can be included with device 100. Similarly, by reversing the orientation of sliding straps 506 or 508 through channels 500-504, device 100 can easily be used on either a left or a right arm.

Figure 10:
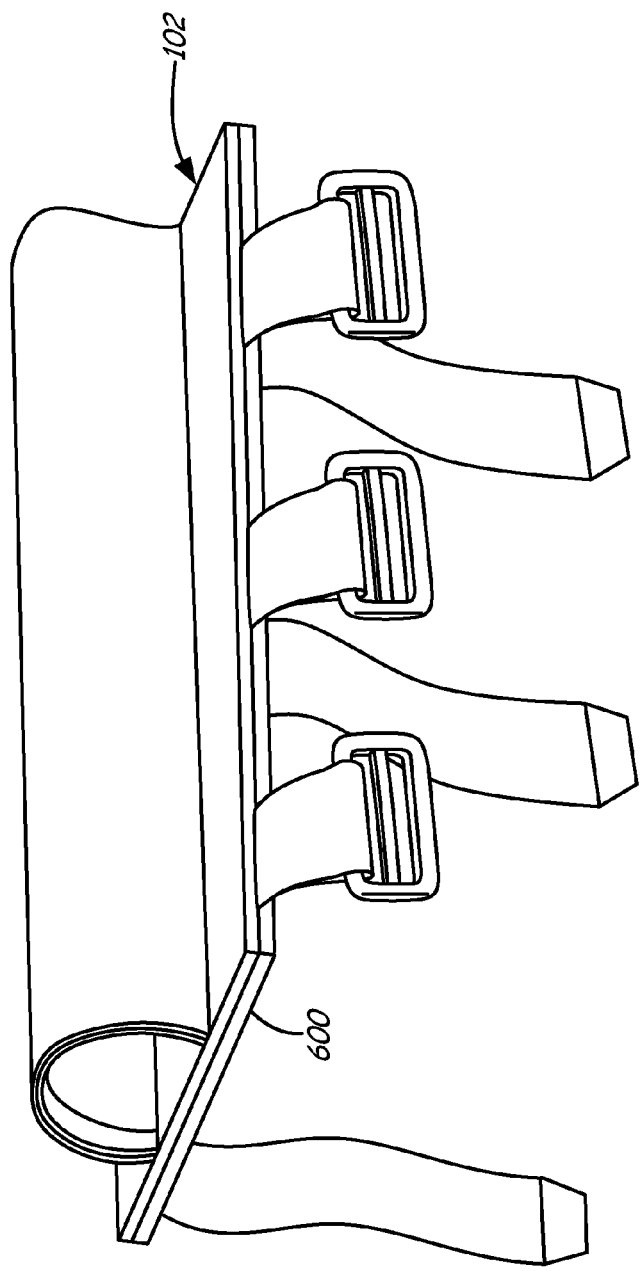
FIG. 10 illustrates an embodiment of the assist device in which a forearm engaging layer of the assist device is formed of a soft material, such as terry cloth, or another padded material.

FIG. 10 shows another embodiment of device 100. In the embodiment shown in FIG. 10, portion 102 is formed of only a single layer of material. However, an additional layer of material 600 is provided for engagement with the user's forearm. The additional layer of material 600 can be terry cloth or another soft material which will reduce any type of abrasion or discomfort to the user while wearing device 100. It will be noted, of course, that instead of providing a separate layer 600 of material on portion 102, the surface of portion 102 that engages the forearm of the user can simply be formed using a soft material, and no separate layer 600 is required.

The assist device described herein can be utilized for a wide variety of applications where grip assistance is desired. Examples of items that can be accommodated by the assist device include, but are not limited to, golf clubs, paint brushes, rakes, shovels, brooms, kitchen utensils, pots and pans, hunting equipment, fishing rods, to name a few.

Figure 11:
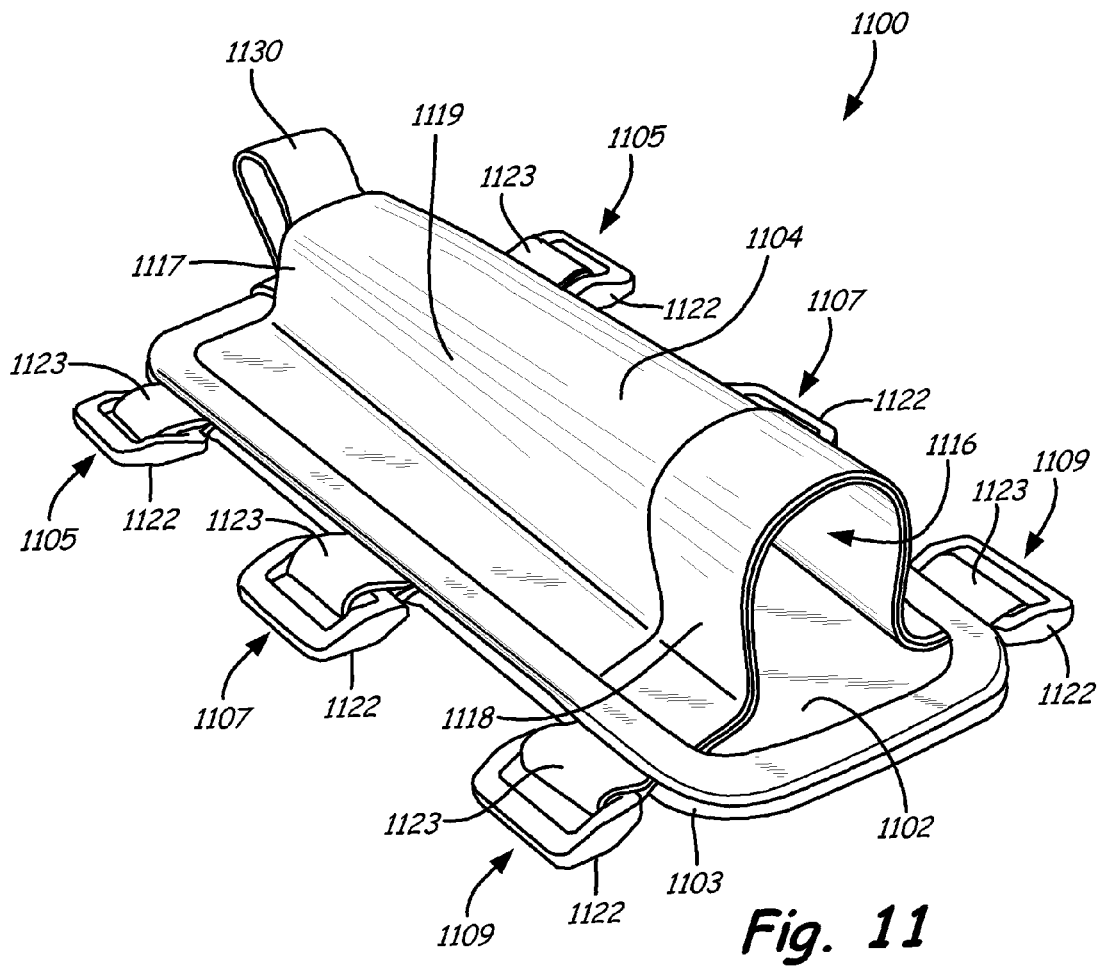
FIG. 11 is a perspective view of an assist device in accordance with one embodiment.

FIG. 11 is a perspective view illustrating one embodiment of an assist device 1100. Assist device 1100 includes a forearm engaging portion 1102 and a pouch or sleeve 1104. Assist device 1100 is configured to assist a user in grasping or manipulating an item with a handle. For example, in one embodiment assist device 1100 is configured to be secured to a user and utilized to assist the user in grasping an item, for instance in a manner similar to that discussed above with respect to FIGS. 2-8.

A first end of pouch 1104 includes a handle receiving opening 1116 and a second end of pouch 1104 comprises a closed end 1117. In one embodiment, pouch 1104 and opening 1116 are similar to pouch 104 and opening 116 illustrated in FIG. 1.

In the embodiment illustrated in FIG. 11, forearm engaging portion 1102 is formed of one or more layers of material. In one example, forearm engaging portion 1102 is rigid, or semi-rigid, and is substantially planer when device 1100 is not attached to a user's arm. For example, portion 1102 can be somewhat flexible allowing portion 1102 to deform, to some extent, to a contour of the user's forearm.

Handle receiving opening 1116 is sized to receive handles of interest to the user and is illustratively formed such that it retains its shape, even when no grip or handle is inserted through it, within pouch 1104. In the embodiment illustrated in FIG. 11, opening 1116 defined by a reinforcement element 1118. In one example, reinforcement element 1118 is formed of material(s) similar to reinforcement element 118, illustrated in FIG. 1. For instance, reinforcement element 1118 can be formed of a material that has a greater rigidity than the material used to form a portion 1119 of pouch 1104.

Assist device 1100 can also include a layer of material 1103 provided for engagement with the user's forearm. Layer 1103 can include materials such as, but not limited to, the materials described above with respect to layer 600.

Assist device 1100 can include a plurality of fastening straps (not shown in FIG. 11). The fastening straps are configured to attach to fasteners (illustratively buckles) attached to portion 1102. In the embodiment illustrated in FIG. 11, assist device 1100 includes pairs of buckles (illustratively three buckle pairs 1105, 1107, 1109). Each buckle pair 1105, 1107, 1109 comprises at least two buckles 1122 attached on opposing sides of assist device 1100. Each buckle pair 1105, 1107, 1109 is configured to receive one of the fastening straps. In one embodiment, each buckle 1122 is attached to portion 1102 using a loop 1123, which can be formed of a material that is the same as or different from portion 1102. In one embodiment, loops 1123 are formed of a flexible material that allows movement of buckles 1122.

In accordance with one embodiment, assist device 1100 can include indicia related to a characteristic of a user, or potential user, of assist device 1100. For example, a portion of the assist device 1100 (such as, but not limited to, reinforcement element 1118) can be color-coded to indicate a particular ailment, disorder, disease, or other characteristic, etc. related to the user (e.g., a cause that the user supports). For instance, "awareness" colors are sometimes used to indicate such things as arthritis (e.g., the color blue) and strokes (e.g., the color red). Alternatively, or in addition, assist device 1100 can be color-coded to indicate a particular characteristic or feature of the device itself. For example, device 1100 can be color-coded to indicate that the device 1100 is especially designed for persons having a particular ailment, disorder, disease, or other characteristic, etc.

Figure 12:
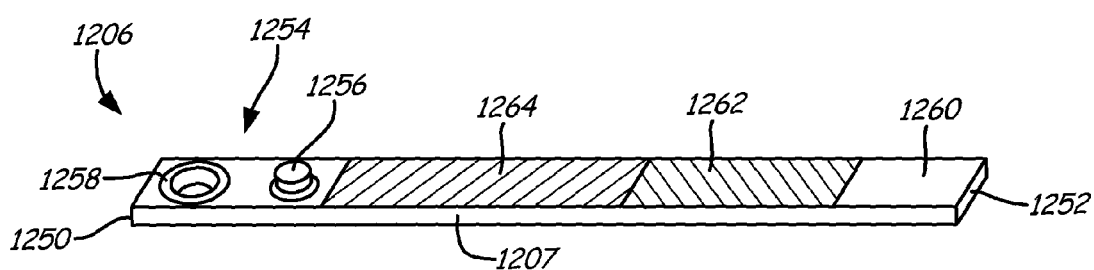
FIG. 12 is a perspective view of a fastening strap, under one embodiment.

FIG. 12 illustrates a fastening strap 1206, under one embodiment. Fastening strap 1206 includes a first end 1250 and a second end 1252. In one example, fastening strap 1206 comprises a base layer 1207 that is formed of a flexible material. A portion of fastening strap 1206 proximate end 1250 is configured to be inserted through and secured to a first buckle 1122. The second end 1252 is configured to be inserted through another buckle 1122 to form a loop, such as that illustrated in FIGS. 3 and 4, for accommodating a user's arm.

Fastening strap 1206 comprises a snap fastener 1254 positioned proximate first end 1250. Snap fastener 1254 comprises a male connector 1256 and a corresponding female connector 1258. To secure first end 1250 to a buckle 1122 of assist device 1100, the first end 1250 is inserted through the buckle 1122 and the end 1250 is folded back such that female connector 1258 engages and secures to male connector 1256. It is noted that snap fastener 1206 is one example of a fastener that can be utilized. Other fastening mechanisms, such as, but not limited to, hook and loop fabric and the like, can be utilized.

The second end 1252 comprises a tab portion 1260 that is inserted through a buckle 1122 (on an opposing side) of assist device 1100. Tab 1260 is inserted through the buckle 1122 and is folded back to secure fastening strap to the buckle 1122. As shown in FIG. 12, a first portion 1262 of fastening strap 1206 is provided with one part of a fastening mechanism, such as hook and loop fabric. A second portion 1264 of fastening strap 1206 is provided with another portion of the fastening mechanism, such as hook and loop fabric. It is noted that other types of fastening mechanisms can be used and are within the scope of the concepts described herein.

A plurality of fastening straps 1206 can be secured to the buckles of each buckle pair 1105, 1107, 1109, forming loose loops through which the user can insert and advance the user's hand. In one embodiment, the process of securing assist device 1100 to a user's arm can be similar to the process described above with respect to FIGS. 3-5. The straps can be tightened (or loosened) around the user's arm by pulling or retracting the strap through the buckle and pressing mechanisms 1262 and 1264 together. Further, by reversing the orientation of the straps on device 1100 (i.e., moving the end 1250 having fastener 1254 from one side of device 1100 to another) device 1100 can easily be adjusted to accommodate the left or right arm. It noted that this is one example of securing and using assist device 1100 and is not intended to limit the scope of the concepts described herein.

Figure 13:
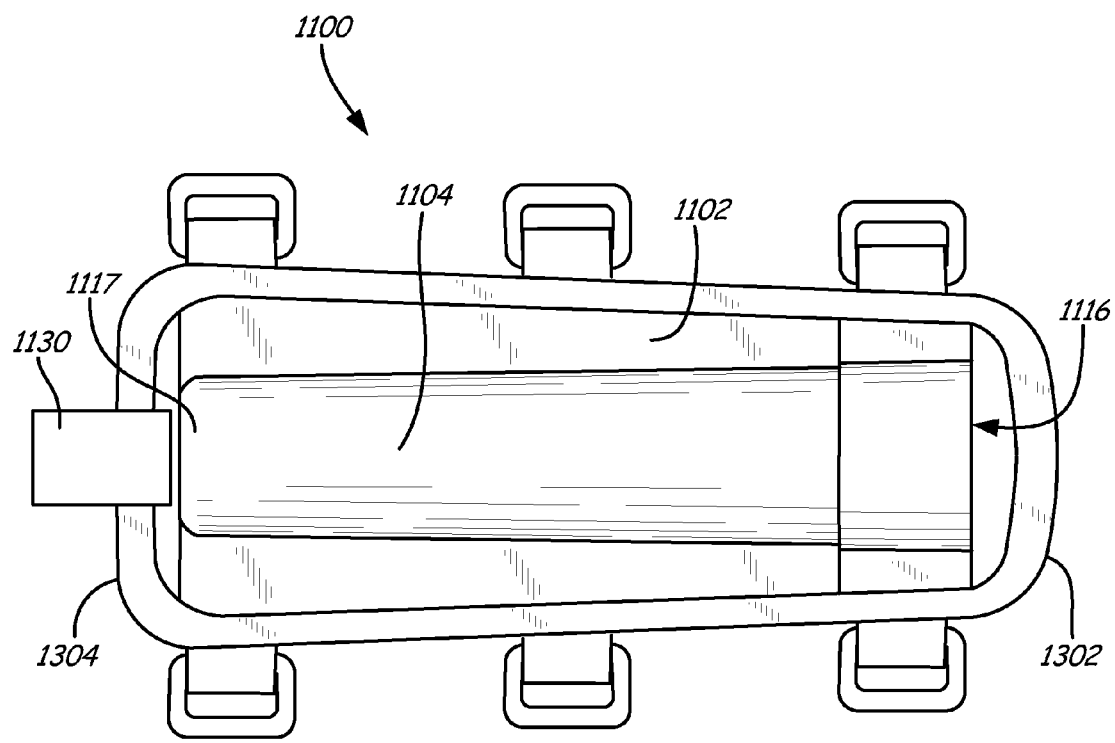
FIG. 13. is a top view of the assist device illustrated in FIG. 11.
Figure 14:
FIG. 14 is a side view of the assist device illustrated in FIG. 11.

FIGS. 13 and 14 are top and side views, respectively, of assist device 1100. As illustrated, the end of pouch 1104 comprising opening 1116 has a larger cross section than the second, closed end 1117 of pouch 1104. Further, a first end 1302 of forearm engaging portion 1102 has a smaller width than a second end 1304, to accommodate the shape of a user's forearm, for instance.

Further, as illustrated in FIGS. 11, 13, and 14, assist device 1100 can include a tab 1130 that extends from portion 1102. Tab 1130 is formed of a loop of material and can comprise flexible, rigid, and/or semi-rigid materials. Tab 1130 extends beyond a top surface of pouch 1104 and is configured to enable a user to grip assist device 1100 using the user's teeth, for example, which can aid the user in positioning assist device 1100 on the user's forearm.

While embodiments described herein are discussed in the context of a device for assisting those who have difficulty grasping items, it is noted that the disclosed assist device can also be utilized by individuals who do not lack adequate grip strength. For example, the assist device can be utilized by a person having adequate grip strength as an aid in lifting items, for example to take stress off of an individual's elbows, shoulders, and/or back, etc.

Moreover, while embodiments described herein are discussed in the context of an assist device configured to be worn on a forearm of a user, it is noted that the assist device can also be worn on other parts of a user's body. For example, the assist device can be worn on an upper arm, leg, ankle, foot, etc. of the user.

Although the present invention has been described with reference to preferred embodiments, workers skilled in the art will recognize that changes may be made in form and detail without departing from the spirit and scope of the invention.

What is claimed is:

1. An assist device comprising:
    a generally planar, deformable, forearm engaging support member having first and second opposed edges, a first side configured to engage a user's forearm, and a second side facing a direction generally opposite the first side;
    a flexible elongate sleeve including a first material disposed on the second side of the support member between the first and second opposed edges, the flexible elongate sleeve having a first end, a second end, and a length extending between the first and second ends, the first end defining an opening sized to receive a portion of an elongate handle such that an end of the elongate handle is disposed within the flexible elongate sleeve, wherein the first material is configured to deform to accommodate, and frictionally engage, the portion of the elongate handle when the portion of the elongate handle is inserted by the user into the flexible elongate sleeve, and wherein the elongate sleeve comprises a reinforcement element including a second material having a greater rigidity than the first material and disposed about a majority of a periphery of the opening of the elongate sleeve to define a generally C-shaped opening; and
    a connection system disposed on the first and second edges of the support member and including a plurality of straps configured to removably attach the assist device to the user's forearm.

2. The assist device of claim 1, wherein the flexible elongate sleeve is tapered along the length of the sleeve from the first end to the second end.

3. The assist device of claim 1, wherein the second material comprises an insert configured to retain a shape of the opening of the elongate sleeve.

4. The assist device of claim 1, wherein the support member is flexible and configured to deform to a contour of user's forearm.

5. The assist device of claim 1, wherein the connection system comprises buckle pairs, each buckle pair being configured to receive one of the straps, and including a first buckle attached to the first edge of the support member and a second buckle attached to the second edge of the support member.

6. The assist device of claim 1, wherein each of the plurality of straps comprises:
    releasable fastening mechanisms disposed on first and second portions of the strap and configured to releasably attach the first and second portions of the strap together; and
    a tab portion at an end of the strap and spaced from the first and second portions of the strap and not including the releasable fastening mechanisms.

7. The assist device of claim 6, wherein the releasable fastening mechanisms comprises hook and loop fabric.

8. The assist device of claim 1, and further comprising a tab extending away from the support member, the tab being attached to at least one of the support member and elongate sleeve.

9. The assist device of claim 8, wherein the tab extends beyond a plane defined by a top surface of the elongate sleeve.

10. The assist device of claim 8, wherein the tab is attached to the second side of the support portion proximate the second end of the elongate sleeve.

11. The assist device of claim 1, wherein the reinforcement element has a different color than the first material.

* * * * *